United States Patent [19]

Meyers et al.

[11] Patent Number: 4,842,857

[45] Date of Patent: Jun. 27, 1989

[54] GLYPHOMICINS A AND B

[75] Inventors: Edward Meyers, East Brunswick; William L. Parker, Pennington, both of N.J.

[73] Assignee: E. R. Squibb and Sons, Inc., Princeton, N.J.

[21] Appl. No.: 861,803

[22] Filed: May 12, 1986

[51] Int. Cl.$^4$ .......................... A61K 35/74; C12P 1/06
[52] U.S. Cl. ..................................... 424/116; 424/118; 435/169
[58] Field of Search ................. 424/116, 118; 435/169

[56] References Cited

PUBLICATIONS

Antimicrobial Agents & Chemotherapy, 1965, "Moenomycin, a New Antibiotic, I. Fermentation and Isolation", Wallhauser et al.
Antimicrobial Agents & Chemotherapy, 1965, "Moenomycin, a New Antibiotic, II. Characterization and Chemistry", Huber et al.
Antimicrobial Agents & Chemotherapy, 1965, "Moenomycin, a New Antibiotic, III. Biological Properties", Wasielewski et al.
Antimicrobial Agents & Chemotherapy, 1965, "Moenomycin in Animal Nutrition", Bauer et al.

*Primary Examiner*—Jerome D. Goldberg
*Attorney, Agent, or Firm*—Lawrence S. Levinson; Robert E. Lee, Jr.

[57] ABSTRACT

Cultivation of a strain of the microorganism Micromonospora sp. A.T.C.C. No. 53481, yields the novel antibiotic substance glyphomicin, which is a mixture of glyphomicin A and glyphomicin B.

2 Claims, 4 Drawing Sheets

GLYPHOMICINS A AND B

SUMMARY OF THE INVENTION

Cultivation of a strain of the microorganism Micromonospora sp. SC 10469, which has been deposited in the American Type Culture Collection as A.T.C.C. No. 53481, yields the novel antibiotic substance glyphomicin. Glyphomicin has been analyzed and found to be made up of two components which have been designated glyphomicin A and glyphomicin B. These compounds, and their pharmaceutically acceptable salts, are phosphoglycolipid antibiotics that are active against gram-positive bacteria.

DETAILED DESCRIPTION OF THE INVENTION

The Microorganism

Figure 1:
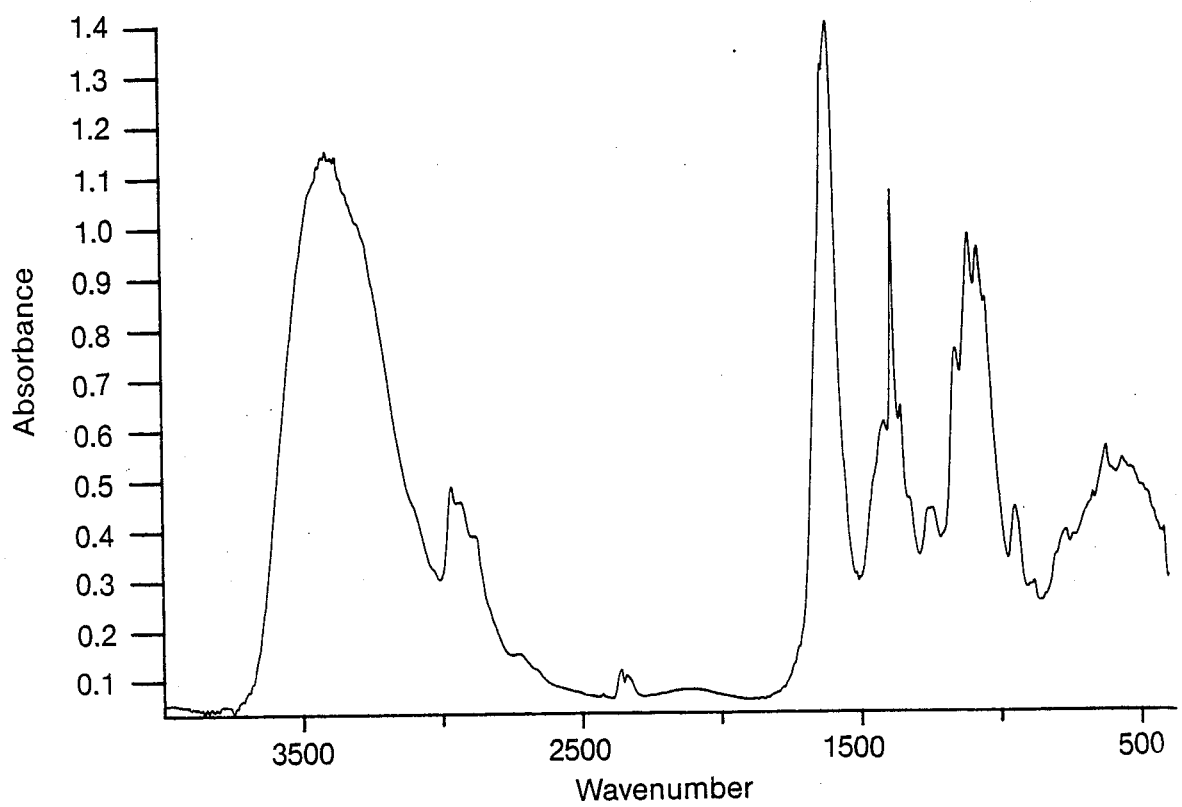
FIG. 1 shows the infrared spectrum of glyphomicin A as the sodium salt in potassium bromide.

The microorganism used for the production of glyphomicin A and B is a species of Micromonospora isolated from the soil. A subculture of the organism may be obtained from the American Type Culture Collection, Rockville, Md. Its accession number in the repository is A.T.C.C. No. 53481. In addition to the specific microorganism described and characterized herein, it should be understood that mutants of the microorganism (e.g., mutants produced through the use of x-rays, ultraviolet radiation or nitrogen mustards) can also be cultivated to produce glyphomicin A and B.

Isolation of Micromonospora sp. SC 10469 from a soil sample in which it is present can be accomplished by first shaking the soil sample in sterile distilled water and plating it on a nutrient agar medium having the following composition:

|  | Grams |
| --- | --- |
| Soluble starch | 10 |
| Casein (Vitamin free) | 0.3 |
| KNO$_3$ | 2 |
| NaCl | 2 |
| K$_2$HPO$_4$ | 2 |
| MgSO$_4$.7H$_2$O | 0.05 |
| CaCO$_3$ | 0.02 |
| FeSO$_4$.7H$_2$O | 0.01 |
| Agar | 20 |
| Distilled water to 1,000 ml | |

The medium is adjusted to pH 7.0 and sterilized at 121° C. and 15 psi for 30 minutes. The plated soil sample is incubated for 7 to 10 days at 28° C.

After the incubation period, colonies of Micromonospora sp. A.T.C.C. No. 53481 are isolated from the plated soil. The organism does not form a true aerial mycelium. Spores are borne singly at the ends of simple sporophores appearing in clusters that are arranged monopodially. The spores are about 1.0 micron in diameter and by electron microscopy the spore surface is seen to be smooth. Hydrolysates of purified cell walls contain meso-diaminopimelic acid, glycine, xylose and arabinose. The mode of spore attachment to the hyphae and the cell wall constituents characterize this organism as a member of the genus Micromonospora.

The cultural characteristics of Micromonospora sp. A.T.C.C. No. 53481 on various media are as follows:

| Cultural Characteristics on Various Media* | | |
| --- | --- | --- |
| Media | 14 Days | 21 Days |
| Micromonospora Maintenance Agar** | Growth is moderate to abundant; colonies are raised and wrinkled. Colors*** range from light tan (3 gc) to light amber (3 lc)-cinnamon (3 le). Sporulating areas are dark brown and of granular texture. Reverse is indistinct; no soluble pigment. | No change except sporulating areas became black and moist but not viscid or granular. |
| Bennett's Agar | Growth is weak; colonies are minute, amber butterscotch (3 lc). Reverse is the same; no soluble pigment. | Growth is poor, colonies are small. |
| Tomato Paste-Oatmeal Agar | Growth is moderate; colonies are small, in shades of orange with dark brown centers (russet orange, 4 pc). Reverse is indistinct; no soluble pigment. | Growth is moderate; colony surface is dark brown to black; dry granular texture. Reverse is indistinct; no pigment. |
| Glucose Asparagine Agar | Growth is poor; pinpoint colonies with dark glistening centers. No distinctive reverse color or soluble pigment. | No change from 14 days. |

*Plates incubated at 28° C.
**Composition in grams per liter: beef extract, 3; tryptone, 5; yeast extract, 5; soluble starch, 24; dextrose, 1; agar, 15; and tap water, one liter.
***Color designations and color chip numbers are from the Color Harmony Manual (Container Corp. of America, 1958) and the ISCC-NBS method of designating colors and color names (National Bureau of Standards, Cir. 533, 1955).

The physiological characteristics of Micromonospora sp. A.T.C.C. No. 53481 are as follows:

| Physiological Characteristics | | |
| --- | --- | --- |
| Proteolysis | Milk plate | Positive clearing |
|  | Gelatin plate | Positive clearing |
| Starch hydrolysis |  | Positive clearing |
| Acid tolerance | Potato plug | No growth |
|  | Potato plug with CaCO$_3$ | Growth |
| NaCl tolerance* | Growth up to 5% NaCl | |
| Melanin production | Negative on sodium caseinate-tyrosine agar | |
| Temperature | Optimal growth between 30° C. and 37° C. | |

*NaCl tolerance is determined in a basal medium containing yeast extract, 1%; soluble starch, 2%; agar, 1.5%; distilled water and the appropriate concentration of NaCl.

The carbohydrate utilization pattern of Micromonospora sp. A.T.C.C. No. 53481 is determined in the basal medium of Leudemann and Brodsky (Antimicrobial Agents and Chemotherapy, 1964:47-52, 1965) consisting of: yeast extract, 0.5%; CaCO$_3$, 0.1% and agar, 1.5% in distilled water. Test carbohydrates are added to a final concentration of 1%, except for glycerol, which is added to a final concentration of 2%. The carbohydrate utilization characteristics of Micromonospora sp. A.T.C.C. No. 53481 are as follows:

| Carbohydrate Utilization of Micromonospora sp. A.T.C.C. No. 53481 | |
|---|---|
| Carbohydrate | Growth* |
| Basal medium | − |
| Glucose | + |
| Glycerol | − |
| Mannitol | − |
| Inositol | − |
| D-Arabinose | + |
| Rhamnose | − |
| Raffinose | − |
| Melibiose | + |
| Sucrose | + |
| Fructose | + |
| Lactose | + |

*−: growth of the organism is not obtained using the listed carbohydrate as the sole carbon source
+: growth of the organism is obtained using the listed carbohydrate as the sole carbon source Production of the Antibiotic Micromonospora sp. A.T.C.C. No. 53481 produces a mixture of antibiotics (glyphomicin A and B) each component of which possesses activity against gram-positive bacteria. To form these antibiotics, according to the preferred methodology, Micromonospora sp. A.T.C.C. No. 53481 is grown at, or near 25° C., under submerged aerobic conditions in an aqueous nutrient medium containing assimilable carbohydrate and nitrogen sources. The fermentation is carried out for approximately 168 to 288 hours, preferably about 240 hours, at the end of which time the mixture of antibiotics has been formed.

After the fermentation is complete, the mycelium, containing most of the antibiotic, is separated by filtration or centrifugation. The antibiotic is extracted from the mycelial cake with tetrahydrofuran-water, 1:1, at pH 8 to 9, obtained by adjustment with concentrated ammonium hydroxide. The extract is concentrated in vacuo to about one tenth of the fermentation volume. The resulting concentrate is mixed with pyridine and the antibiotic mixture sorbed on a column of a strongly basic, macroporous anion exchange resin, such as Bio-Rad AG MP-1, in the acetate form. Glyphomicin A and glyphomicin B are eluted from the column, in that order, using a gradient of ammonium acetate in pyridine-water, 2:1. Fractions containing glyphomicin A are combined and concentrated in vacuo. Ammonium acetate is then removed by partition chromatography on Sephadex G-25 in pyridine-water, 1:1, or in pyridine-0.1M ammonium hydroxide, 1:1. Removal of solvent from the active fractions gives crude glyphomicin A. Crude glyphomicin B is obtained from the ion-exchange eluate in the same way. Glyphomicin A and B are each further purified by chromatography on DEAE cellulose, eluting with a gradient of ammonium acetate in pyridine-water, 1:1, and by chromatography on Amberlite XAD-2 resin, eluting with a gradient of acetonitrile in aqueous ammonia. Desalting by chromatography on Sephadex G-25 as above gives the ammonium salts of glyphomicins A and B.

For large scale isolation, glyphomicins A and B are further purified by chromatography on DEAE cellulose eluting with a gradient of ammonium acetate in propanol-butanol-pyridine-water, 2:2:1:5 followed by desalting by chromatography on Amberlite XAD-2 resin with a gradient of acetonitrile in aqueous ammonia to give the ammonium salts.

The ammonium salts of glyphomicins A and B are converted to the sodium salts by chromatography on MCI Gel CHP20P resin with a gradient of acetonitrile in pH 7.8 sodium phosphate buffer followed by rechromatography of the active effluent on the same resin with a gradient of acetonitrile in water.

The glyphomicins are acidic antibiotics that are unstable to acid, moderately unstable in neutral aqueous solution, and most stable at higher pH. They are thus best handled as dry salts (e.g., the ammonium or sodium salt as prepared above) or as solutions maintained at pH 8 to 9. Pharmaceutically acceptable basic salts of the glyphomicins are readily prepared using ion-exchange techniques.

The following examples further illustrate the preparation and isolation of glyphomicins A and B.

EXAMPLE 1

Production of Glyphomicin Mixture

A 10 liter batch of Micromonospora sp. A.T.C.C. No. 53481 was fermented in a 14 liter glass tank with the medium and operating conditions described below:

Stage 1—Inoculum: Culture of Micromonospora sp. A.T.C.C. No. 53481, preserved by storage under liquid nitrogen and grown out on a medium of the following composition:

| | Grams |
|---|---|
| Beef extract | 3 |
| Tryptone | 5 |
| Yeast extract | 5 |
| Soluble starch | 24 |
| Glucose | 1 |
| Agar | 15 |
| Distilled water to 1,000 ml | |

The medium was sterilized at 121° C. and at 15 lbs. steam pressure for 30 minutes.

Growth from slants was used to inoculate 100 ml portions of medium contained in 500 ml Erlenmeyer flasks. The composition of the germination medium was:

| | Grams |
|---|---|
| Toasted nutrisoy flour | 15 |
| Soluble starch | 15 |
| Glucose | 50 |
| CoCl$_2$.6H$_2$O | 0.005 |
| CaCO$_3$ | 10 |
| Distilled water to 1,000 ml | |

The medium was sterilized at 121° C. and at 15 lbs. steam pressure for 30 minutes.

Germination flasks were incubated at 25° C. for 72 hours on a rotary shaker operating at 300 rpm with a two inch throw.

Stage 2 —Inoculum: 500 ml from the first stage.

| Medium: | Grams |
|---|---|
| Pharmamedia | 30 |
| Soluble starch | 15 |
| Glucose | 30 |
| CaCO$_3$ | 7 |
| Distilled water to 1,000 ml | |

The medium was sterilized at 121° C. and at 15 lbs. steam pressure for 30 minutes.

Ten liters of medium containing the inoculum in a 14 liter glass vessel was incubated for 240 hours. During incubation, the broth was agitated at 350–400 rpm and aerated at the rate of 3.5 to 4.0 liters of air per minute.

EXAMPLE 2

Isolation of Glyphomicin A and Glyphomicin B

The fermentation broth from two fermentors, totaling 19 liters, was centrifuged, giving 2.5 kg of mycelial cake. The cake was suspended in 7.5 liters of tetrahydrofuran water, 1:1, and the slurry was adjusted to pH 8.0 with concentrated ammonium hydroxide. Solids were separated by centrifugation and reextracted twice with five liter portions of tetrahydrofuran-water, 1:1. The combined extract was concentrated in vacuo below 45° C. to 0.6 liters, and the concentrate was diluted with 1.2 liters of pyridine and filtered. A 1.3 liter portion of the filtrate was applied to a 2.5×48 cm column of Bio-Rad AG MP-1 resin, acetate form, in pyridine-water, 2:1. The column was then eluted at 3 ml per minute with 500 ml of pyridine-water, 2:1, followed by a linear gradient prepared from four liters of pyridine-water, 2:1, and four liters of 0.3M ammonium acetate in pyridine-water, 2:1. During the gradient elution, 20 ml fractions were collected and assayed against *Staphylococcus aureus* FDA 209P. Glyphomicin A was found in fractions 160 to 200 and glyphomicin B was found in fractions 264 to 370.

Fractions 160 to 200 containing glyphomicin A, were combined and concentrated in vacuo, giving 14 grams of residue. This residue was dissolved in 17 ml of pyridine-water, 1:1, and applied to a 2.5×76 cm column of Sephadex G-25 in pyridine-water, 1:1. The column was eluted with this solvent at 2 ml per minute until all of the antibiotic had emerged. Active fractions were combined and concentrated in vacuo, giving 0.54 grams of crude glyphomicin A.

Fractions 264 to 370 containing glyphomicin B, were combined and concentrated in vacuo, giving 36 grams of residue. This residue was dissolved in 53 ml of pyridine-water, 1:1, and applied to a 2.5×76 cm column of Sephadex G-25 in pyridine-water, 1:1. The column was eluted with this solvent at 2 ml per minute until all of the antibiotic had emerged. Active fractions were combined and concentrated in vacuo, giving 0.50 grams of crude glyphomicin B.

EXAMPLE 3

Glyphomicin A, ammonium salt

Crude glyphomicin A, 0.54 grams, obtained as described in Example 2, was dissolved in 5 ml of pyridine-water, 1:1, and applied to a 2.5×32 cm column of Whatman DE52 diethylaminoethyl cellulose, acetate form, packed in pyridine-water, 1:1. The column was eluted at 3 ml per minute with 200 ml of pyridine-water, 1:1, and then with a linear gradient prepared from two liters of pyridine-water, 1:1, and two liters of 0.25M ammonium acetate in pyridine-water, 1:1. During the gradient, 20 ml fractions were collected and assayed against *S. aureus* FDA 209P. The antibiotic was found in fractions 56 to 72. Active fractions were combined and concentrated in vacuo, giving 1.2 grams of syrup. This was dissolved in 3 ml of pyridine-0.1M aqueous ammonium hydroxide, 1:1, and applied to a 2.5×76 cm column of Sephadex G-25 in the same solvent system. The column was eluted at this system at 2 ml per minute until all of the antibiotic had emerged. Active fractions were combined and concentrated in vacuo giving 47 mg of the partially purified ammonium salt of glyphomicin A.

EXAMPLE 4

Glyphomicin B, ammonium salt

Crude glyphomicin B, 0.50 grams, obtained as in Example 2, was dissolved in 15 ml of pyridine-water, 1:1, and applied to a 2.5×38 cm column of Whatman DE52 diethylaminoethyl cellulose, acetate form, in the same solvent. The column was eluted at 4 ml per minute with 200 ml of pyridine-water, 1:1, and then with a linear gradient prepared from two liters of pyridine-water, 1:1 and two liters of 0.2M ammonium acetate in pyridine-water, 1:1. During the gradient elution, 20 ml fractions were collected. By assay against *S. aureus* FDA 209P, the antibiotic was found in fractions 152 to 182. Active fractions were combined and concentrated in vacuo giving three grams of residue. This residue was dissolved in pyridine-water, 1:1 and applied to a 2.5×76 cm column of Sephadex G-25 in the same solvent. The column was eluted with this solution at 2 ml per minute until the antibiotic had emerged. Active fractions were combined, made basic with ammonium hydroxide, and concentrated in vacuo. Lyophilization of the residue from water gave 180 mg of glyphomicin B as the ammonium salt.

EXAMPLE 5

Production of Glyphomicin Mixture

A 250 liter batch of Micromonospora sp. A.T.C.C. No. 53481 was fermented in a 100 gallon stainless steel vessel with the medium and operating conditions described below:

Stage 1—Inoculum: Culture of Micromonospora sp. A.T.C.C. No. 53481 was preserved by storage in liquid nitrogen and grown out on agar slants of the following composition:

|  | Grams |
| --- | --- |
| Beef extract | 3 |
| Tryptone | 5 |
| Yeast extract | 5 |
| Soluble starch | 24 |
| Glucose | 1 |
| Agar | 15 |
| Cold tap water to 1,000 ml | |

The medium was sterilized at 121° C. and at 15 lbs. steam pressure for 30 minutes.

Surface growth from a slant was suspended in 11.0 ml of a 0.01% sodium lauryl sulfate solution and 1 ml of this suspension was used as the source of inoculum.

| Medium: | Grams |
| --- | --- |
| Toasted nutrisoy flour | 15 |
| Glucose | 50 |
| Soluble starch | 15 |
| $CoCL_2.6H_2O$ | 0.005 |
| $CaCO_3$ | 10 |
| Water to 1,000 ml | |

The medium was sterilized at 121° C. and at 15 lbs. steam pressure for 30 minutes.

One hundred ml of this medium in a 500 ml Erlenmeyer flask was incubated 72 hours on a rotary shaker at 25° C. The shaker was operated at 300 rpm with a two inch throw.

Stage 2—Inoculum: 100 ml from the first stage. Medium: Same as stage 1. Erlenmeyer flasks containing 1,500 ml of medium and inoculum per 4,000 ml Erlenmeyer flask were incubated at 25° C. on a rotary shaker. The shaker was operated at 125 rpm with a two inch throw.

Stage 3—Inoculum: 6,000 ml from Stage 2.

| Medium: | Grams |
|---|---|
| Pharmamedia | 30 |
| Soluble starch | 15 |
| Glucose | 30 |
| CaCO₃ | 7 |
| Ucon LB-625 | 1 |
| Distilled water to 1,000 ml | |

The medium was sterilized at 121° C. and at 15 lbs. steam pressure for 30 minutes.

A 250-liter batch of medium and inoculum in a 100 gallon stainless steel fermentation vessel was incubated for 240 hours at 25° C. During incubation, the broth was agitated at 155 rpm and aerated at the rate of 10 cubic feet per minute.

EXAMPLE 6

A 110-liter batch of whole fermentation broth from Example 5 was mixed with 8.8 kg of Hyflo Supercel and filtered. The wet cake (26.4 kg) was extracted with three 60-liter portions of tetrahydrofuran-water, 1:1, adjusting the pH of the slurry to 9.0 with 58% ammonium hydroxide. The combined extract (142 liters) was concentrated to 10.9 liters in vacuo, maintaining the pH between 9 and 10 by the addition of ammonium hydroxide and adding n-butanol as necessary to control foaming.

The concentrate was diluted with an equal volume of pyridine and filtered. Ten liters of the filtrate were passed through a column prepared from 50 grams of Bio-Rad AG MP-50 resin, 200 to 400 mesh, NH₄⁺ form. The effluent was then applied to a 5×67 cm column of Bio-Rad AG MP-1 resin, 100 to 200 mesh, acetate form, packed in pyridine-water, 1:1. The column was washed with two liters of pyridine-water, 2:1, and then eluted with a linear gradient prepared from four liters of pyridine-water, 2:1, and four liters of 0.5M ammonium acetate in pyridine-water, 2:1, at 5 ml per minute, collecting 20-ml fractions. Fractions were assayed by paper-disc, agar-diffusion assay against S. aureus FDA 209P. Fractions 181 to 242, containing chiefly glyphomicin A, were combined and concentrated in vacuo, adding 0.1M ammonium hydroxide as needed to keep the solution basic. Fractions 243 to 400, containing chiefly glyphomicin B, were similarly combined and concentrated. The remaining extract concentrate was chromatographed in the same way. The glyphomicin A concentrates from the two runs were combined, as were the glyphomicin B concentrates.

Crude glyphomicins A and B were desalted by partition chromatography on Sephadex G-25 (fine) in pyridine-0.1M ammonium hydroxide, 1:1. The glyphomicin B concentrate was applied to a 5×37 cm column and eluted at 4 to 8 ml per minute, collecting 20 ml fractions. Fractions 11 to 55 contained antibiotic and fractions 31 to 108 contained ammonium acetate. Fractions 31 to 55 were combined and rechromatographed to get complete separation of the antibiotic from the salt.

Desalted crude glyphomicin B in 400 ml of pyridine-water, 1:1, was applied to a 5×40 cm column of Whatman DE52 cellulose, acetate form, in pyridine-water, 1:1. The column was eluted at 5 ml per minute with 900 ml of pyridine-water, 1:1, and was then eluted with a linear gradient prepared from 4 liters of pyridine-water, 1:1, and 4 liters of 0.2M ammonium acetate in pyridine-water, 1:1. The column was overloaded and active fractions that were eluted before the start of the gradient were combined and rechromatographed. The active fractions from the gradient were combined, desalted on Sephadex G-25 (as above except that pyridine-0.01M ammonium hydroxide, 1:1, was used) and rechromatographed on Whatman DE52 cellulose as above to give, after desalting, 3.56 g of purer glyphomicin B. The crude glyphomicin A was chromatographed as above on Whatman DE52 cellulose to give, after desalting, 2.39 g of purer glyphomicin A.

Desalted glyphomicin B from the DEAE cellulose chromatography was chromatographed on a 5×61 cm column of Whatman DE52 cellulose, acetate form. The column was eluted at 5 ml per minute first with 250 ml of propanol-butanol-pyridine-water, 2:2:1:5, and then with a linear gradient prepared from 6 liters of this mixture and 6 liters of 0.2M ammonium acetate in the same mixture, collecting 20 ml fractions. Active fractions (341 to 530) were combined and concentrated in vacuo, giving 18 g of syrup. The syrup was dissolved in 25 ml of 0.01M ammonium hydroxide and applied to a 2.5×25 cm column of Amberlite XAD-2 resin, 100 to 200 mesh, packed in 0.01M ammonium hydroxide. The column was eluted at 2 ml per minute, first with 80 ml of 0.01M ammonium hydroxide, and then with a linear gradient prepared from 800 g of 0.01M ammonium hydroxide and 800 g of acetonitrile-0.1M ammonium hydroxide, 9:1, collecting 20 ml fractions during gradient elution. The paper-disc, agar-diffusion assay showed a major peak of bioactivity eluting in fractions 26 to 37. These fractions were combined, concentrated in vacuo, and the residue lyophilized from water, giving 1.39 g of glyphomicin B as the ammonium salt.

The desalted glyphomicin A from the DEAE cellulose chromatography was rechromatographed on Whatman DE52 cellulose, using a gradient of ammonium acetate in propanol-butanol-pyridine-water, 2:2:1:5, and was then chromatographed on Amberlite XAD-2 resin with a gradient of acetonitrile in 0.01M ammonium hydroxide as described above for glyphomicin B. This gave 0.3 g of glyphomicin A as the ammonium salt.

A sample of glyphomicin B ammonium salt that was dried in vacuo at 50° C. for 9 hours gave the following elemental analysis (%): C, 53.38; H, 7.60; N, 4.96; P, 2.43.

Chromatography on Whatman No. 1 paper in the descending mode with the upper phase of butanol-acetic acid-water, 4:1:5 (v/v/v), gave $R_f$ values of 0.46 and 0.30 for the ammonium salts of glyphomicins A and B, respectively. Thin-layer chromatography on Gelman ITLC, type SA, eluting with n-propanol-2M ammonium hydroxide, 7:3, gave $R_f$ values of 0.59 and 0.51 for the ammonium salts of glyphomicins A and B, respectively.

EXAMPLE 7

A 0.55 g sample of glyphomicin B, ammonium salt (partially decomposed on storage) was dissolved in acetonitrile-water-pH 7.8 sodium 0.05M phosphate buffer, 1:3:1 (5 ml) and chromatographed on a 2.5×20 cm column of MCI GEL CHP20P resin (75 to 150 micron) eluting at 2 ml per minute with a linear gradient prepared from 2 liters of the same mixture and 2 liters of acetonitrile-water-pH 7.8 buffer, 3:1:1. The antibiotic, monitored by absorbance at 247 nm and assayed against S. aureus FDA 209P, eluted between 1,400 and 1,800 ml. The active effluent was concentrated and the residue rechromatographed on the same column eluting at 2.5 ml per minute with 200 ml of water followed by a linear gradient prepared from 500 ml of water and 500 ml of water-acetonitrile, 1:1. The antibiotic, monitored by absorbance at 247 nm, elutes between 280 and 610 ml. The active effluent was concentrated in vacuo, and the residue lyophilized from water to give glyphomicin B, 41 mg, as the sodium salt.

A 0.3 g sample of the ammonium salt of glyphomicin A (partially decomposed on storage) was chromatographed on MCI CHP20P resin with acetonitrile-pH 7.8 sodium phosphate buffer and the active effluent concentrated and rechromatographed on MCI Gel CHP20P resin with an acetonitrile-water gradient as described for glyphomicin B. The active effluent was concentrated in vacuo and the residue lyophilized from water to give glyphomicin A, 41 mg, as the sodium salt.

Characterization data for the sodium salts of glyphomicins A and B are as follows:

| Characterization Data for the Sodium Salts of Glyphomicins A and B | | |
|---|---|---|
| | Glyphomicin A | Glyphomicin B |
| Physical form | white amorphous solid | white amorphous solid |
| Melting point | >260° C. | >260° C. |
| MW of the free acids* | 1172 | 1348 |
| UV max, nm ($E^{1\%}$) | | |
| $H_2O$ | 246(202) | 246(185) |
| 0.01 M NaOH | 246(198) | 246(184) |
| 0.01 M HCl | 242(169) | 242(159) |
| IR (KBr)cm$^{-1}$ (FIGS. 1 & 2) | 3403, 1609, 1384, 1157, 1109, 1077, 1050 | 3435, 1622, 1384, 1156, 1106, 1077, 1049 |
| Paper electrophoresis, $M_{NOS}$** | 0.53 | 0.65 |
| HPLC k'*** | 8.6 | 3.1 |
| Paper chromatography**** | 0.31 | 0.28 |
| Elemental analysis***** | | |
| % C | 47.69 | 42.07 |
| H | 6.30 | 5.50 |
| N | 2.06 | 1.71 |
| P | 2.0 | 1.75 |
| $[\alpha]_D$ in DMSO-$d_6$D$_2$O, 6:1 | +11 ± 1°****** | −2.3 ± 0.7°******* |

*Based on fast atom bombardment mass spectra.
**In formamide-pH 7 sodium 0.09 M phosphate buffer, 3:2. Mobilities are relative to vitamin B12 (0.00) and p-nitrobenzenesulfonate anion (1.00).
***Waters 10μ C$_{18}$ Radial Pac column eluting with acetonitrile-0.05 M ammonium bicarbonate, 9:16 (v/v).
****Descending on Whatman No. 1 paper, eluting with butanol-acetic acid-water, 4:1:5 (v/v/v), upper phase.
*****The sodium salt of glyphomicin A contained 6.3% water and the sodium salt of glyphomicin B contained 7.7% water by Karl Fischer tritration. Samples were not dried prior to elemental analysis and found values are uncorrected. Approximate analyses for sodium were performed by flame atomic absorption on the intact antibiotics and after ashing. Glyphomicin A gave values of 7.1 and 6.7% and glyphomicin B gave values of 15.2 and 11.6% Na.
******T = 24° C., c = 0.23 g/100 ml.
*******T = 23° C., c = 0.3 g/100 ml.

Biological Activity

Two-fold broth dilution assays against a panel of microorganisms showed the following results:

| | MIC (μg/ml) Glyphomicin | |
|---|---|---|
| Organism | A* | B* |
| Staphylococcus aureus FDA 209P | 0.03 | 0.02 |
| Streptococcus pyogenes C$_{203}$ | 0.05 | <0.004 |
| Escherichia coli A.T.C.C. 10536 | NT** | 75 |
| Escherichia coli SC 8294*** | NT | >100 |
| Pseudomonas aeruginosa SC 8329 | NT | >100 |
| Candida albicans SC 5314 | NT | >100 |

*Ammonium salts, prepared in Example 6
**NT means test not done
***Organism from Squibb Culture Collection, E. R. Squibb & Sons, Inc., Princeton, New Jersey The materials referred to above by tradename are described below:

Bio-Rad AG MP-1 resin: Macroreticular styrene-divinylbenzene copolymer resin with —CH$_2$N$^+$(CH$_3$)$_3$ groups attached. Bio-Rad Laboratories.

Bio-Rad AG MP-50 resin: Macroreticular styrene-divinylbenzene copolymer resin with —SO$_3^-$ groups attached. Bio-Rad Laboratories.

Sephadex G-25: Cross-linked dextran gel. Pharmacia Fine Chemicals, Inc.

Whatman DE52: Diethylaminoethyl cellulose. Whatman Chemical Separation Ltd.

Amberlite XAD-2 resin: Macroreticular styrene-divinylbenzene copolymer resin. Rohm and Haas Company.

MCI GEL CHP20P resin: Macroreticular styrene-divinylbenzene copolymer resin. Mitsubishi Chemical Industries Ltd.

Ucon LB-625: Polyalkylene glycol fluid. Union Carbide Corp.

Hyflo Supercel: Diatomaceous earth. Johns-Manville.

Gelman ITLC, type SA: Polysilicic acid gel impregnated glass fiber sheets. Gelman Sciences, Inc.

Waters 10μ C$_{18}$ Radial Pac Column: C$_{18}$-silica gel HPLC column. Waters Associates, Inc.

Pharmamedia: Nitrogen source derived from cotton seed meal. Traders Protein.

Figure 3:
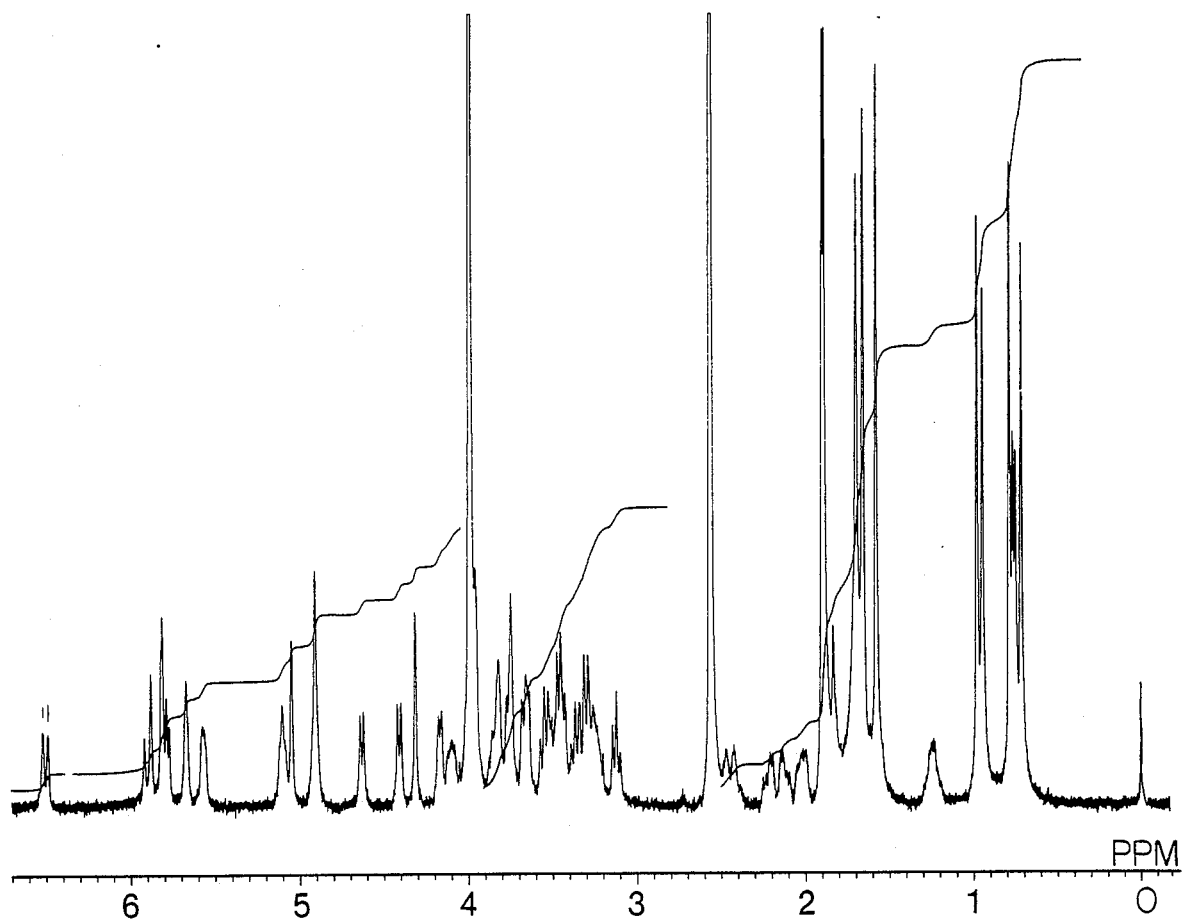
FIG. 3 shows the 400 MHz $^1$H NMR spectrum of glyphomicin A as the sodium salt in deuterated dimethylsulfoxide:deuterated water (4:1).

What is claimed is:

1. Glyphomicin A, or a pharmaceutically acceptable salt thereof, the sodium salt of which has the infrared spectrum in potassium bromide as shown in FIG. 1, the 400 MHz $^1$H NMR spectrum as shown in FIG. 3, and having the approximate elemental analysis C, 47.69%, H, 6.30%, N, 2.06%, P, 2.0%.

Figure 2:
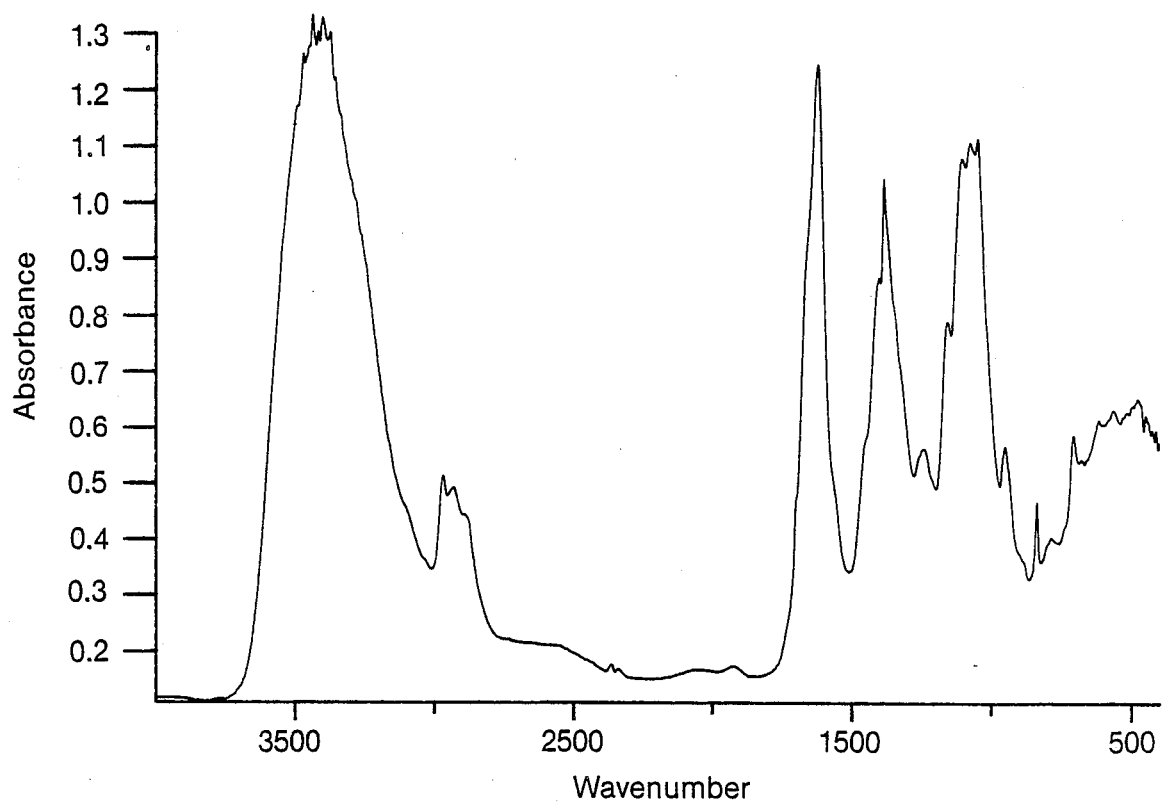
FIG. 2 shows the infrared spectrum of glyphomicin B as the sodium salt in potassium bromide.
Figure 4:
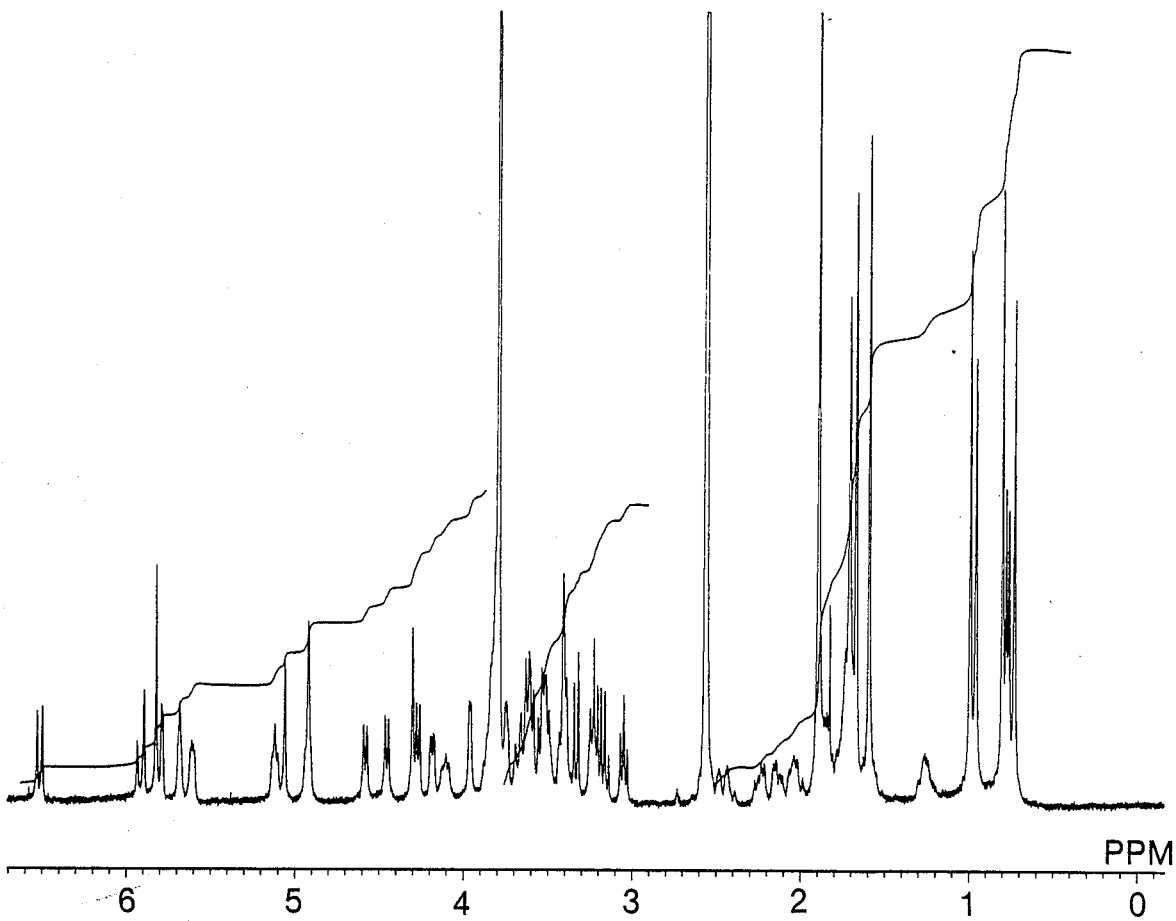
FIG. 4 shows the 400 MHz $^1$H NMR spectrum of glyphomicin B as the sodium salt in deuterated dimethylsulfoxide:deuterated water (6:1).

2. Glyphomicin B, or a pharmaceutically acceptable salt thereof, the sodium salt of which has the infrared spectrum in potassium bromide as shown in FIG. 2, the 400 MHz $^1$H NMR spectrum as shown in FIG. 4, and having the approximate elemental analysis C, 42.07%, H, 5.50%, N, 1.71%, P, 1.75%.

* * * * *